United States Patent [19]
Nenniger

[11] Patent Number: 5,959,194
[45] Date of Patent: Sep. 28, 1999

[54] METHOD AND APPARATUS FOR MEASUREMENT AND PREDICTION OF WAXY CRUDE CHARACTERISTICS

[76] Inventor: John Nenniger, 4512 Charleswood Dr. N.W., Calgary, Alberta, T2L 2E5, Canada

[21] Appl. No.: 09/017,727

[22] Filed: Feb. 3, 1998

[51] Int. Cl.⁶ .............................. G01N 11/00; G01N 5/00; G01N 17/00
[52] U.S. Cl. ...................... 73/53.01; 73/53.05; 73/61.62; 73/61.71
[58] Field of Search .............................. 73/53.01, 53.05, 73/61.71, 61.41, 61.65, 61.62

[56] References Cited

U.S. PATENT DOCUMENTS

| | | | |
|---|---|---|---|
| Re. 33,468 | 12/1990 | Brindak | 73/61.2 |
| 2,645,461 | 7/1953 | Brown et al. | 257/4 |
| 3,008,324 | 11/1961 | Rayford et al. | 73/17 |
| 3,848,187 | 11/1974 | Rohrback et al. | 324/65 CR |
| 4,544,489 | 10/1985 | Campbell et al. | 210/709 |
| 4,781,893 | 11/1988 | Dickakian | 422/69 |
| 5,036,699 | 8/1991 | Fikentscher et al. | 73/61.2 |
| 5,257,528 | 11/1993 | Deguoy et al. | 73/53.01 |
| 5,370,799 | 12/1994 | Oddo et al. | 210/696 |
| 5,419,185 | 5/1995 | Chimenti et al. | 73/54.01 |
| 5,492,005 | 2/1996 | Homan et al. | 73/61.62 |
| 5,708,196 | 1/1998 | Tolvanen et al. | 73/53.05 |
| 5,753,802 | 5/1998 | Falkler | 73/61.62 |

*Primary Examiner*—Hezron Williams
*Assistant Examiner*—J. David Wiggins

[57] ABSTRACT

A method and apparatus for the measurement and prediction of waxy crude characteristics is disclosed. The method is for treating oil samples having at least some wax, by the steps of isolating a sample of crude to be tested, testing the sample by subjecting the sample to known amounts of at least one of pressure, shear rate and temperature, and evaluating the wax in the tested sample. In another embodiment the apparatus includes at least one of a pressure chamber to hold an oil sample, a pressure control to control pressure of the sample, a temperature control to control the oil temperature, a shear rate control to control shear rates in the sample and a sensor and data acquisition system to measure particle characteristics of said sample, to simulate field conditions which waxy crudes may be subjected to.

18 Claims, 2 Drawing Sheets

--- CONTROL LINE
-·-·- SENSOR LINE

METHOD AND APPARATUS FOR MEASUREMENT AND PREDICTION OF WAXY CRUDE CHARACTERISTICS

FIELD OF THE INVENTION

This invention relates to the field of hydrocarbon production and most particularly relates to the production of hydrocarbons such as oils from underground formations, where the oils contain in either solution or suspension or both, traces of wax.

BACKGROUND OF THE INVENTION

The production of hydrocarbons such as oil and gas is important for both economic and strategic reasons. The recovery of oil or gas from a particular reservoir is determined by the economics of operation. If the revenue is less than the operating costs, then the well will be either shut in (to wait for higher prices, better production technology, etc.) or the well may be plugged with concrete and abandoned. To maximize cash flow and profits it is common to try to produce as much oil as possible, without damaging the well.

One known problem which can restrict the flow of oils from a well is the deposition of wax in the flow paths causing restrictions and choking off flow. As waxy crudes cool down, during transport through piping or other means from the reservoir to the refinery, paraffin wax will precipitate. The precipitated paraffins cause numerous problems such as flow obstruction due to the deposition of plugging deposits in pipelines, poor pumpability due to high viscosity and difficulty breaking water/oil emulsions that may inadvertently form during production.

In some environments such as offshore pipelines and tubulars each incident of plugging due to wax deposition can cost millions of dollars. It has been recently reported that 17 such incidents occurred in the Gulf of Mexico during a one year period. The economic incentives to prevent plugging depositions are high.

To date there is no reliable technique to predict rates of wax deposition. Lab measurements of deposition rates seldom correlate to measured rates in the field. The factors which control the solubility of the paraffin in crude are fairly straightforward to measure analytically and model with thermodynamics. However, wax deposition and plugging is usually less severe in highly waxy crudes and more severe in less waxy crudes. There are pipelines which carry extremely waxy crude and do not require any wax deposit removal through use of for example "pigging" or chemical solvent flushing/cleaning.

Similarly, measurement of waxy crude rheology (viscosity and yield strength) is not very reliable. Rheology data measured by different labs can differ by 10 fold for the same oil sample. The simulation (or lack of) "temperature/time/shear history" (that is the exact combination of events that a crude may be subjected to during production from the reservoir and transportation to a refinery) is usually used to explain the lack of consistent results between field measurements and lab measurements. Yield strengths may vary by more than 1000 fold depending on what pretreatment conditions the crude or produced hydro carbons may be subjected to.

Why are the waxy crude properties so difficult to measure reliably? Some reasons include:

1) The dominant mechanism for wax precipitation appears to be formation of suspended solids. The suspended solids are fairly innocuous and are carried along in the oil as a slurry. Typically only a small proportion (i.e., perhaps less than 1%) of the precipitated wax forms adherent deposits which can cause flow blockages or restrictions. Thus, paraffin precipitation occurs via two competing pathways, ire., suspended solids vs adherent deposits.

2) The factors which control the proportion of adherent wax vs. suspended solids are more complex. For example, if there is an inventory of suspended waxy solids then these solids can absorb paraffin supersaturations due to their relatively large surface areas (see Canadian patent 1,289,497 Nenniger, J. *Process for Inhibiting Formation of Wax Deposits*). For example, 100 ppm of waxy solids (1 micron in diameter) in crude oil have 10 times more surface area than the inside wall of the 2⅞" tubing in which they are transported. Thus, the suspended solids inhibit the formation of adherent deposits. Therefore the proportion of wax precipitating to form adherent deposits is a nonlinear function of the inventory of suspended solids.

3) In lab scale simulations, it is not possible to simulate all large scale phenomena simultaneously. For example, if we match the shear rate in the oil in both the lab and the field, then the Reynold's number cannot be matched at the same time (unless the lab apparatus is dimensionally identical to the field).

To date there has not been any systematic attempt to characterize waxy solids other than to note that they are present. Thus to date, research efforts have only examined part of the deposition mechanism so prediction based on lab scale equipment has not been reliable.

BRIEF SUMMARY OF THE INVENTION

What is desired is a method and apparatus for reliable characterization and prediction of crude oil properties which could allow optimization of transport/process parameters to minimize capital and operating expenses. Such a method and apparatus to reliably predict wax deposition rates could reduce development and operating costs and allow economic oil recovery from marginal oil pools or underground formations.

What is further desired is a method and apparatus for characterizing any suspended solids in the crude to provide additional parametric data to allow for more accurately simulated field processes in lab scale equipment. Furthermore said apparatus must be small, robust and portable so that it can be readily transported to provide measurements on production fluids in the field. This will preferably include characterization of particle nucleation and growth phenomena. For example, shear rates, cooling rates, paraffin supersaturation, loss of light ends, diffusion rates, temperature gradients, heat fluxes, nuclei such as dirt or asphaltene miscels are expected to influence wax particle size, particle shape, particle concentration and particle surface area.

What is further desired is a method and apparatus to determine and correlate the deposition rate of adherent wax to any influence of these factors (including particle size, particle shape, particle concentration, particle surface area).

The present invention comprehends a quantitative approach to determining and isolating the processes affecting the waxy crude characteristics. It is a desire of the present invention to thereby reduce both capital and operating expenditures for oil well owners and operators by allowing operators and designers to make informed cost/benefit decisions about the optimum techniques, designs, layouts, configurations, fixtures, and elements of pipeline and other transportation elements to facilitate optimizing the transport/process for any a particular crude having wax components.

The present invention therefore most preferably comprehends a small bench scale apparatus in which one can control the factors which affect wax particle nucleation and growth in a way that most preferably simulates full scale production systems. Since there are many factors involved, and the specific influence of any particular one of the factors, let alone any combinations of events or factors are not presently understood such control is desired. Further, the present invention comprehends benchmarking the particles generated in the apparatus against the particles generated in the field to develop control correlations.

Thus the present invention comprehends an approach which is analogous to solving a multidimensional nonlinear equation;—a trial and error procedure is used until the correct answer is obtained. In more specific terms, what is preferred is to systematically vary one or more control factors or parameters (temperature, shear rate, pressure, heat flux, etc.) to determine at least one set of appropriate experimental conditions which reasonably mimic the particle characteristics observed in the field.

The parameters which determine the particle inventory may vary from oil to oil. The present invention comprehends making a benchmark of the lab generated particles produced in the apparatus against a number of actual production systems to gain confidence. For example, for some crude oil production systems shear nucleation may be the dominant particle formation mechanism whereas some other oils already contain many nuclei (i.e. asphaltenes) and thus are not as sensitive to shear rate.

The present invention further comprehends a method and apparatus to be used to do studies on oil samples for which production systems/flow lines have not been built. In this manner the present invention comprehends measuring the effect of various design options on the rate of wax deposition.

Additionally the present invention comprehends a method and apparatus to systematically examine the effect of various chemical additives such as crystal modifiers and dispersants to determine effectiveness and optimal concentrations.

Therefore, there is provided according to one aspect of the present invention an apparatus for characterizing waxy crudes comprising:

a chamber to hold a fluid sample;

a means to provide controlled shear rates in the fluid within said chamber;

a means to provide cooling/heating to the fluid within said chamber;

a means to regulate the temperature gradients/heat flux in the fluid within said chamber;

a means to regulate the pressure/composition of the fluid within said chamber;

a means to introduce particles into the fluid within said chamber;

a means to measure deposit accumulation rates on the surfaces of said chamber;

a means to withdraw fluid samples from said chamber;

a means to measure fluid rheology within said chamber;

a means to characterize the particles the fluid within said chamber including probes and sensors p1 a means for numerical calculation of said characteristics using said sensors and probes comprising external computational devices and software a means for control of said temperature, heat flux, shear rates, pressure/composition in said chamber using external signal processing devices, computational devices and software.

BRIEF DESCRIPTION OF THE DRAWINGS

Reference will now be made, by way of example only, to preferred embodiments of the invention as illustrated in the accompanying drawings and in which.

DETAILED DESCRIPTION OF THE PREFERRED EMBODIMENTS

Figure 1:
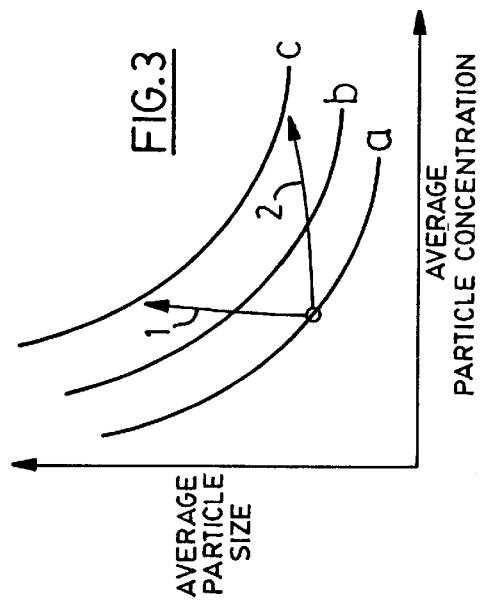
FIG. 1 illustrates the thermodynamic relationship between the temperature and the amount of insoluble paraffin in a crude oil.

FIG. 1 shows the thermodynamic relationship between the temperature and the amount of insoluble paraffin in a crude oil at equilibrium. As the oil temperature decreases, the amount of insoluble paraffin in the oil increases as shown by points 'a', 'b', and 'c'. This relationship is relatively straightforward and can be measured in the lab and modelled with thermodynamic models such as NWAX™ developed by Nenniger Engineering Ltd. of Calgary, Alta. Can.

Figure 2:
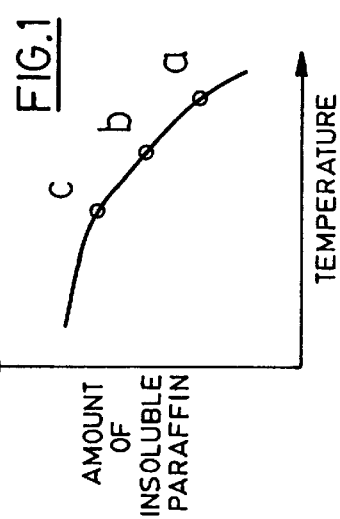
FIG. 2 illustrates the relationship between particle size and particle concentration for a crude oil at three different temperatures.

However, observations in the lab have revealed that the size and number of wax particles in the crude oil can vary widely. Thus, FIG. 2 shows that thermodynamic equilibrium at 'a' results in a curve. At equilibrium, a particular crude oil sample will lie somewhere on curve 'a', but the location is indeterminate unless one has obtained additional information.

Figure 3:
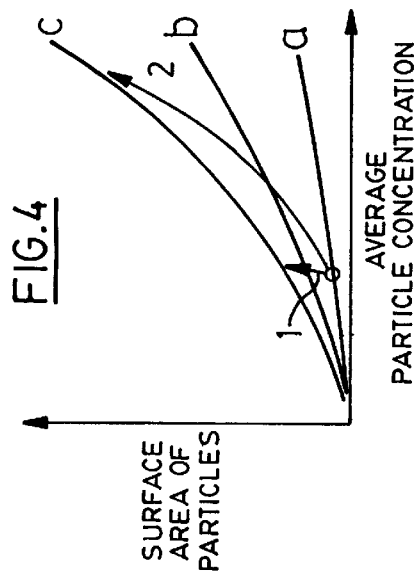
FIG. 3 illustrates the changes in particle size and particle concentration for two different oil transportation processes.

FIG. 3 shows why the location on the curve is indeterminate. As the oil is cooled as shown from 'a' through 'b' to 'c', the particle size distribution will change. Two different paths are illustrated in FIG. 3. Path 1 can be used to illustrate, by way of example only, cooling in the absence of shear. Thus, the existing particles grow larger and very few new particles are formed. Path 2 can be used to illustrate, by way of example only, cooling in the presence of high shear. In this case the high shear leads to shear nucleation and the formation of many particles. Thus, FIG. 3 illustrates moving from thermodynamic equilibrium at 'a' to thermodynamic equilibrium at 'c', yet what results are two fluids (following path 1 and path 2) with very different rheology and wax particle size distributions. Thus, the oil properties at 'c' are a function of both thermodynamics and the particular path.

Thus it is preferred to simulate the temperature/time/shear history (i.e. the path) in order to reproduce the fluid rheology characteristics. Previously this had been difficult because it was not known how to accurately reproduce the path because some factors, such as shear rate profiles in turbulent pipe flow, cannot be accurately simulated in small lab scale equipment.

Figure 4:
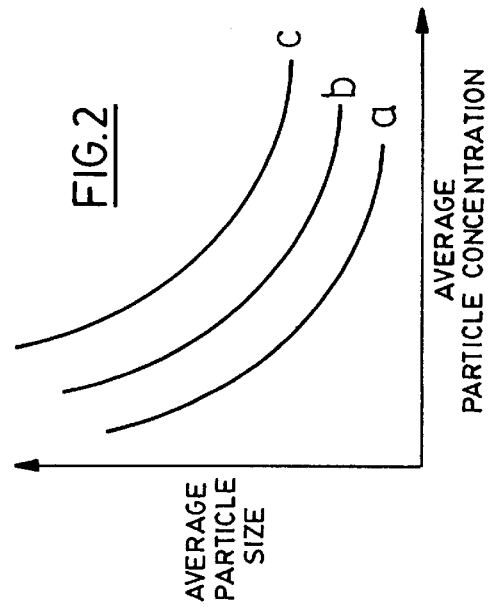
FIG. 4 illustrates the changes in particle surface area for the two different oil transportation processes.

FIG. 4 shows the effect of the different paths on the surface area of the wax particles suspended in the oil. Path 1 results in a very small increase in the surface area of the suspended waxy solids. Path 2 results in a large increase in the surface area of the suspended waxy solids. A consideration of the present invention is the concept that the proportion of paraffin which forms adherent deposits on the walls of a pipeline will be determined by the surface area of the suspended solids vs the surface area of the pipe wall. Thus wax deposition rates at 'c' will be much less for a crude which has followed path '2' instead of path '1'. The dependence of wax deposition rates on path has been previously demonstrated (see Canadian patent 1,289,497 Nenniger, J. *Process for Inhibiting Formation of Wax Deposits*).

Figure 5:
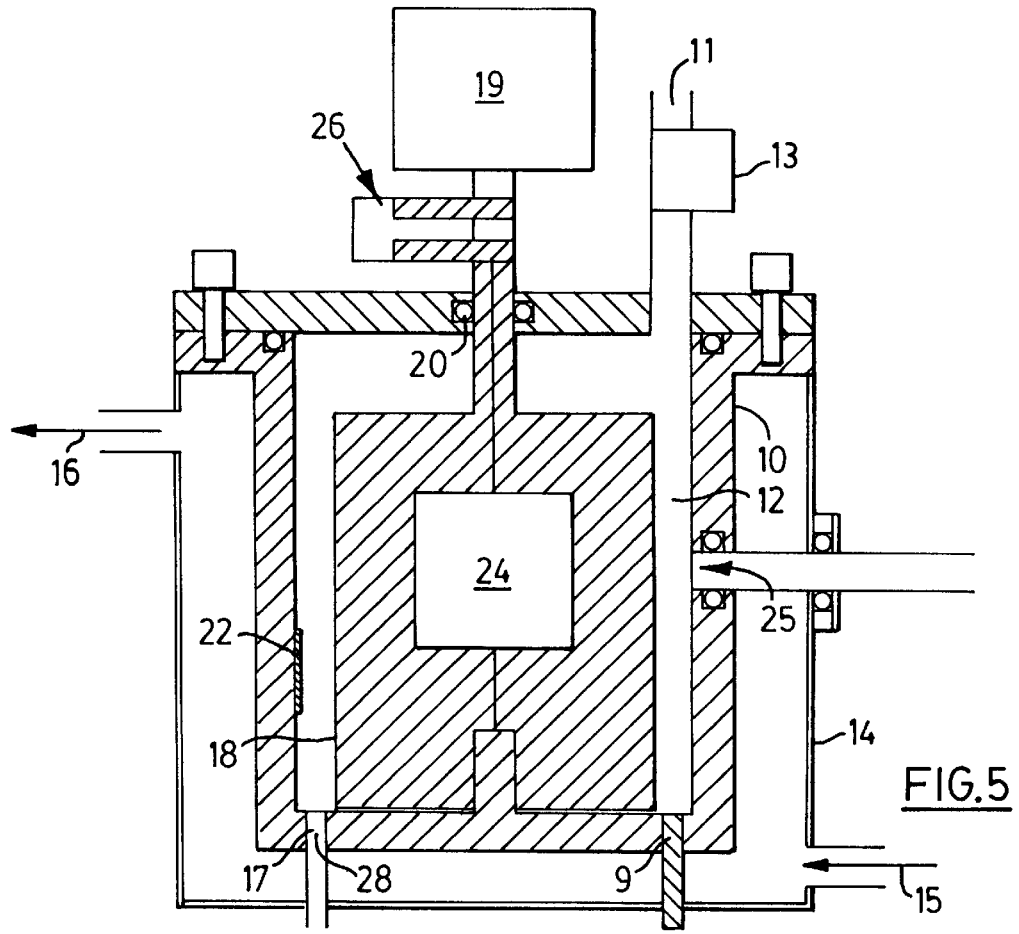
FIG. 5 illustrates a schematic of the invention, a laboratory scale device to simulate different oil transportation processes and measure the consequent particle characteristics, wax deposition rates and rheology of the oil.

FIG. 5 illustrates a schematic of apparatus for measurement and prediction of waxy crude characteristics according to the present invention, which comprises a laboratory scale device to simulate different oil transportation processes as might occur in the field and measure the consequent particle characteristics, wax deposition rates and rheology of the oil. The device consists of a pressure chamber 10, which contains live oil 12 (i.e., oil at a sufficiently high pressure to keep volatile species dissolved). Oil is introduced into the chamber at inlet 11. The pressure in chamber 10 is controlled by a pressure regulator 13. The pressure chamber is surrounded by a water cooled jacket 14 with water inlet and water outlet 16. The oil temperature is measured at 17. A programmable circulating bath 8 such as sold by Cole Parmer is used to provide precise temperature control.

The oil 12 is contained in the annulus between the chamber 10 and a cylindrical bob 18. Although a cylindrical geometry is shown, it would be acceptable to use a cone and plate geometry also. The bob 18 and/or the inside wall of the chamber 10 could have small grooves, ridges or the like to help keep the waxy solids in the oil in suspension and thereby avoid sedimentation. A drain plug 9 allows the oil to flow through the apparatus in case of field sampling. A motor 19 spins the bob 18 at a controlled rate to provide a controlled shear rate in the oil 12. The motor 19 has a rpm sensor, and is similar to those used in viscometers. However, extra torque is required to overcome friction due to the rotating pressure seal 20 around the shaft. Most particle size measurement systems require fluid viscosity data to calculate the particle size distribution. The friction from the pressure seal 20 interferes with torque measurements on the bob 18. Therefore, the shear stress in the oil is measured with a strain gauge type sensor 22 on the inside wall of the chamber, to allow the oil viscosity to be calculated.

A sensor 24 (typically optical or ultrasonic) provides measurements of the particle size distribution in the oil 12. One such system (Microtrac) is manufactured by Honeywell Inc. and uses Doppler shifts from laser backscatter to measure the particle size distribution. This system is preferred because the light penetration is shallow (300 microns) so the technique can be used for black oils. Furthermore this product can be purchased with an external probe which can be inserted into the pressure chamber. Internal standards (i.e. particles) may be added to the oil to provide an independent calibration of the particle size distribution measurement.

To provide heat flux control which is independent of the temperature control, a Thermo Electric Module (TEM) 24 installed in the bob 18. The thermoelectric module 24 is powered by a slip ring arrangement 26 on the shaft of the bob 18. The thermoelectric module 24 is essentially a heat pump which allows a portion of the bob to run cold while another portion runs hot. The TEM 24 might be used in several ways. The TEM 24 could allow the heat flux to be varied independently of a particular cooling rate. However, the TEM 24 would probably be used collect a wax deposit at a particular temperature. There could be several TEMS 24 arranged on the bob 18 so that wax deposits could be collected at several temperatures during one run. Melcor Corporation of Trenton, N.J. manufactures a large variety of TEM's.

It will be appreciated that the wax deposit rate (i.e. deposit thickness) could be measured in several ways. One way would be to drain the oil and open the chamber, and measure the deposit thickness on the bob. The wax deposit could also be sampled for analysis. The deposit thickness may also be electronically measured by means of a magnetic, acoustic or optical type sensor 28. A variety of such sensors are sold by the Paul N. Gardner Company of Pompano Beach, Fla.

Figure 6:
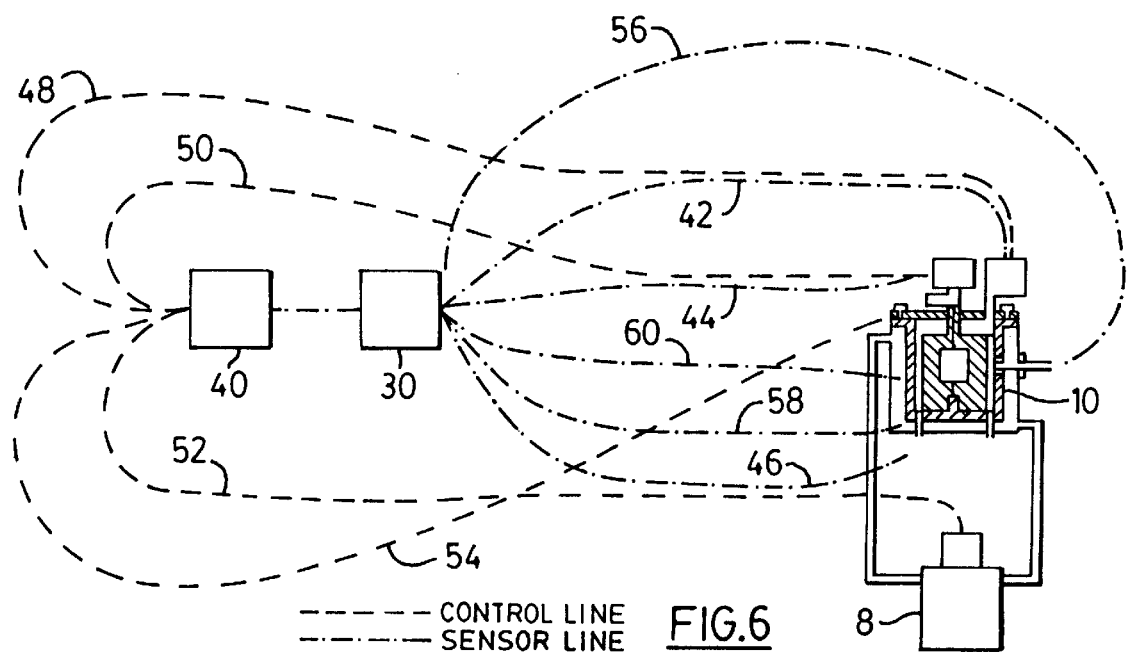
FIG. 6 illustrates a schematic of the data acquisition and control system for the present invention.

FIG. 6 illustrates a schematic of the data acquisition and control system for the present invention. For simplicity, one data acquisition unit 30 and one process control unit 40 are shown. Both functions may be supplied by the same computer, or perhaps several computers would be used to provide the data acquisition. Pressure 42, shear rate 44 and temperature 46 would be measured by sensors in the pressure cell 10. Pressure 48, shear rate 50 and temperature 52 would be controlled in a manner to simulate the temperature/time /shear history in a particular well or pipeline. Heat fluxes could also be controlled with the TEM 54. These parameters are expected to determine the path as discussed earlier (FIGS. 3 and 4).

As the oil follows the programmed temperature/time/shear history, data acquisition provides information on the particle size distribution 56, the wax deposit thickness 58 and the shear stress 60 (viscosity) of the oil.

Thus, in summary, while it will be appreciated by those skilled in the art that the present invention does not exactly simulate the field generated temperature time shear history of crude oil in real production systems in bench scale equipment the present invention teaches a method and apparatus to provide additional criteria (with respect to waxy crude particle characteristics) over other systems. In this manner the present invention comprehends simulating the field processes closely enough to establish correlations to field results with appropriate benchmarking against real production crude. Thus, the present invention provides the possibility of additional quality control for lab scale modelling and simulations.

The preferred method of the present invention is analogous to solving a multidimensional nonlinear equation;—a trial and error procedure is used until the correct answer is obtained. In practical terms, what is required is to systematically vary the control parameters (temperature, shear, pressure, heat flux, etc.) to discover the appropriate experimental conditions which reliably reproduce the particle characteristics observed in the field. Thus, it will be preferred to benchmark the invention using oil samples obtained from different locations in a production system. Benchmarking will allow field correlations to be formed and to determining the significance of the various parameters. The present invention further comprehends using correlated information to enable more accurate simulation of production systems which are in the design stage, than were heretofore available. In this manner the present invention allows capital expenses to be minimized by identifying optimal design choices from a wax deposition and rheology of fluid point of view.

Thus by matching these additional constraints (i.e., suspended waxy particle size distribution characteristics) in the lab scale apparatus, this invention will provide more accurate and meaningful wax deposition rate data at reasonable cost, using small oil samples.

The invention will also be useful to determine the impact of operating practices on wax deposition rates and control. The effect of process parameters (shut in times, cold start, flow rate, pressure, etc) can be studied and the usefulness of various production chemicals (i.e. wax dispersants, pour point inhibitors, solvents, demulsifiers, flow improvers, etc) can be determined. Furthermore the invention will be useful to determine the effect of various design options (insulated vs uninsulated pipe, heating, seeding etc.).

It will be appreciated by those skilled in the art that various modifications and alterations can be made to the present invention without departing from the broad scope of the instant invention as defined by the attached claims. Some of these have been discussed above and others will be apparent to those skilled in the art. For example, depending upon the crude oil being evaluated, one or more of the factors of temperature, shear or wax solid size and concentration may be more or less important. Thus, for any given circumstance it may be necessary to only consider the dominant factor or factors and it may be sufficient to leave out a consideration of other factors. However, the present invention is directed broadly to the concept of subjecting a sample of crude to at least one simulated field experience in a manner sufficient to correlate the lab results to field results to form a basis for prediction for future characteristics.

I claim:

1. A method of treating oil samples containing at least some wax, said method comprising:
    isolating from a production system a field sample of crude oil to be tested;
    testing said sample by subjecting said sample to known amounts of at least one of pressure, shear rate and temperature which simulate at least a portion of one or more of a temperature, pressure or shear history of said production system; and
    evaluating the wax deposition thickness from said tested sample over temperature condition that may be inclusive of but also extended beyond the range of cloud point formation.

2. A method of treating oil as claimed in claim 1 whereby said step of evaluating said wax further includes measuring at least one of a wax deposit thickness and a rate of wax deposit accumulation.

3. A method of treating oil as claimed in claim 1 whereby said method includes comparing said wax from said tested sample to wax in field generated samples.

4. A method of treating oil as claimed in claim 1 whereby said method include placing said sample in an apparatus having sensors and a software control system, and wherein said step of testing said sample includes pretreating said oil sample with particles of known characteristics for calibration of the sensors and software.

5. A method of treating oil as claimed in claim 1 whereby said method also includes adding controlled amounts of additives to evaluate their effect on wax deposit removal or inhibition in field simulated conditions.

6. A method of treating oil as claimed in claim 1 whereby said method also includes adding controlled amounts of additives to evaluate their effect on altering a rheology of said sample in field simulated conditions.

7. A method of treating oil as claimed in claim 1 whereby said method also includes subjecting said sample to controlled amounts of at least one of said pressure, shear rate and temperature to simulate field procedures to evaluate an effect of said field procedures on one or more of wax deposit inhibition or removal or rheology modification.

8. A method of treating oil as claimed in claim 1 whereby said method also includes subjecting said sample to controlled amounts of at least one of said pressure, shear rate and temperature to simulate field transportation configurations to evaluate an effect of said field procedures on one or more of wax deposit inhibition or removal or rheology modification.

9. A oil sample testing apparatus for testing waxy crude oil with dissolved and/or suspended wax therein, said comprising:
    one or more of are pressure chamber to hold said oil;
        a pressure control to control said oil pressure;
        a temperature control to control said oil temperature over temperature conditions that may be inclusive of but also extend beyond the range of cloud point formation;
        a shear rate control to control the shear rate in said oil; and
    a surface in said pressure chamber exposed to said oil upon which wax deposition can occur and from which a thickness of wax deposition can be measured for simulating field conditions to which waxy crude oil may be subjected.

10. A oil treating apparatus as claimed in claim 9 further including shear sensors and a data acquisition system to receive data from said shear sensors to measure shear stress in the oil.

11. A oil treating apparatus as claimed in claim 9 further including wax deposit sensors and a data acquisition system to receive data from said deposit sensors to measure wax deposit thickness.

12. A oil treating apparatus as claimed in claim 9 further including means to control heat flux in said oil independent of temperature.

13. A oil treating apparatus as claimed in claim 9 further including means to admit fresh oil samples directly from existing production systems for purposes of benchmarking.

14. A oil treating apparatus as claimed in claim 9 further including means to admit oil containing known particle characteristics, for purposes of calibration of the sensors and software.

15. An oil treating apparatus as claimed in claim 9 whereby chemicals can be studied to determine effectiveness for wax deposit removal or inhibition.

16. An oil treating apparatus as claimed in claim 9 whereby chemicals can be studied to determine their effectiveness for rheology modification.

17. An oil treating apparatus as claimed in claim 9 whereby operating practices can be studied to determine their effectiveness for wax deposit removal or inhibition or rheology modification.

18. An oil treating apparatus as claimed in claim 9 whereby production system design options can be studied to determine their consequences for wax deposit removal or inhibition or rheology modification.

* * * * *